US007638669B2

United States Patent
Casey et al.

(10) Patent No.: US 7,638,669 B2
(45) Date of Patent: Dec. 29, 2009

(54) INTEGRATED PROCESS FOR PRODUCING XYLENES AND HIGH PURITY BENZENE

(75) Inventors: Edward M. Casey, Mount Prospect, IL (US); Patrick J. Silady, Niles, IL (US); Antoine Negiz, Wilmette, IL (US); Gregory R. Werba, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/146,030

(22) Filed: Jun. 25, 2008

(65) Prior Publication Data

US 2008/0262278 A1    Oct. 23, 2008

Related U.S. Application Data

(62) Division of application No. 11/427,111, filed on Jun. 28, 2006, now Pat. No. 7,405,335.

(60) Provisional application No. 60/695,553, filed on Jun. 30, 2005.

(51) Int. Cl.
*C07C 6/12*    (2006.01)
(52) U.S. Cl. .................................. 585/470; 585/475
(58) Field of Classification Search .................. 585/470, 585/475
See application file for complete search history.

(56) References Cited

U.S. PATENT DOCUMENTS

| 3,812,197 | A | 5/1974 | Suggitt et al. | |
|---|---|---|---|---|
| 4,341,914 | A | 7/1982 | Berger | 585/474 |
| 5,877,373 | A | 3/1999 | Zinnen et al. | |
| 6,740,788 | B1 | 5/2004 | Maher et al. | 585/319 |
| 2003/0130549 | A1 | 7/2003 | Xie et al. | |
| 2004/0186330 | A1 | 9/2004 | Kong et al. | 585/319 |
| 2004/0186332 | A1 | 9/2004 | Kong et al. | 585/475 |
| 2008/0262280 | A1 | 10/2008 | Casey et al. | |

OTHER PUBLICATIONS

Robert A. Meyers, *Handbook of Petroleum Refining Processes*, 2d. Edition, 1997, Part 2.
U.S. Appl. No. 12/146,043, filed Jun. 25, 2008, Edward M. Casey et al., USPTO Notice of Allowance mailed Mar. 6, 2009.

*Primary Examiner*—Thuan Dinh Dang
(74) *Attorney, Agent, or Firm*—Maryann Maas

(57) ABSTRACT

Processes and apparatus are provided that provide high yields of xylenes per unit of aromatic-containing feed while enabling a high purity benzene co-product to be obtained without the need for an extraction or distillation to remove $C_6$ naphthenes. The processes of this invention include a transalkylation section and a disproportionation section in the benzene and toluene-containing feed is directly provided to the transalkylation section and in which a benzene recycle loop in the transalkylation section isolates the disproportionation section from $C_6$ naphthenes.

6 Claims, 2 Drawing Sheets

INTEGRATED PROCESS FOR PRODUCING XYLENES AND HIGH PURITY BENZENE

CROSS REFERENCE TO RELATED APPLICATIONS

This application is a Division of copending application Ser. No. 11/427,111 filed Jun. 28, 2006, which application claims priority from Provisional Application No. 60/695,553 filed Jun. 30, 2005, the contents of which are hereby incorporated by reference.

FIELD OF THE INVENTION

This invention pertains to integrated processes for producing xylenes and highly pure benzene from feed streams containing aromatics and non-aromatics and to integrated processes where highly pure benzene can be obtained without resorting to extraction to remove benzene co-boilers.

BACKGROUND OF THE INVENTION

Most new aromatics complexes are designed to maximize the yield of benzene and para-xylene. Benzene is a versatile petrochemical building block used in many different products based on its derivation including ethylbenzene, cumene, and cyclohexane. Para-xylene is also an important building block, which is used almost as exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in part 2 of the Handbook of Petroleum Refining Processes, 2d. Edition, in 1997 published by McGraw-Hill.

In general, a xylene production facility can have various types of processing reactions. One is a transalkylation in which benzene and/or toluene are reacted with $C_9+$ aromatics to form more methylated aromatics. Another is xylene isomerization, which may also include dealkylation, where a non-equilibrium mixture of xylenes is isomerized. The ethylbenzene may be isomerized to xylenes or may be dealkylated to yield, e.g., benzene. And another is disproportionation in which toluene is disproportionated. The disproportionation reaction yields one mole of benzene per mole of xylene produced.

The benzene sought for other chemical processes and for commercial sale is often required to meet stringent purity standards. One major use of benzene is as a feed to make cyclohexane which in turn can be used to make nylons. For this use, the benzene purity demanded is at least about 99.85 mass percent. Other uses of benzene may have different purity demands, but usually the purity must be at least about 99.0, most commonly at least about 99.5, mass percent.

Accordingly, for a xylene production facility to be a viable source of benzene, it must be able to achieve benzene purity. However, the feeds to xylene production units are generally derived from petroleum reforming and contain many impurities including $C_6$ and $C_7$ non-aromatics, including cyclic aliphatics, that are difficult to remove from benzene by distillation and are often referred to as benzene co-boilers. Additionally, benzene co-boilers may be by-products of catalytic unit operations used to make xylenes from other aromatics contained in the various streams in a xylene production facility. Moreover, impurities in the feeds may be deleterious to catalysts used in these unit operations.

Commonly the feed or a fraction of the feed containing benzene and toluene has been subjected to an extraction process to remove non-aromatic components, including benzene co-boilers. The extraction removes components that could adversely affect catalysts in various catalytic unit operations in the facility. And, because the benzene co-boilers have been removed, a benzene stream from the disproportionation can be recovered as a highly pure stream through distillation.

U.S. Pat. No. 6,740,788 to Maher, et al., disclose a process in which the feed to a transalkylation reactor is fractionated in a benzene column prior to being passed to the reactor. The overhead from the column is extracted to remove non-aromatics in a raffinate and highly pure benzene is obtained. The patentees state that the entire feed to the transalkylation reactor need not be subjected to such an extraction process provided that the transalkylation catalyst has been stabilized through the introduction of a metal function.

US 2004/0186330 of Kong, et al., discloses a process for producing xylenes containing a transalkylation section, a disproportionation section and an isomerization section. The disclosure provides for the extraction of non-aromatics from the benzene and toluene-containing portion of the feed. No disclosure is provided about obtaining a benzene product. Benzene from the disproportionation is recycled to the transalkylation section to make toluene.

US 2004/0186332 of Kong, et al., discloses a process for producing xylenes using a disproportionation and transalkylation of toluene and heavy aromatics.

U.S. Pat. No. 4,341,914 to Berger discloses a transalkylation process with recycle of $C_{10}$ alkylaromatics in order to increase yield of xylenes from the process. The transalkylation process is also preferably integrated with a para-xylene separation zone and a xylene isomerization zone operated as a continuous loop receiving mixed xylenes form the transalkylation zone feedstock and effluent fractionation zones.

Integrated processes are desired that maximize the production of xylenes while still enabling high purity benzene to be provided as a product stream without the requirement for an extraction unit operation.

SUMMARY OF THE INVENTION

By this invention, processes are provided that provide high yields of xylenes per unit of aromatic-containing feed while enabling a high purity benzene co-product to be obtained without the need for an extraction or distillation to remove non-aromatics from the feed. The processes of this invention include a transalkylation section and a disproportionation section wherein the benzene and toluene-containing feed is directly provided to the transalkylation section and in which a benzene recycle loop in the transalkylation section isolates the disproportionation section from benzene co-boilers contained in the feed. The highly pure benzene product is obtained exclusively from the disproportionation of toluene.

Hence, in accordance with the broad aspects of the invention, integrated processes for the production of xylenes and highly pure benzene from aromatic feedstocks containing benzene co-boilers comprise:

a. separating by fractionation a benzene and toluene-containing fraction from said feedstock, said fraction containing benzene co-boilers;

b. subjecting said benzene and toluene-containing fraction to transalkylation conditions including the presence of $C_9$ and $C_{10}$ aromatics and a metal-stabilized transalkylation catalyst to provide a transalkylation product stream having a greater concentration of toluene and $C_8$ aromatics;

c. separating by fractionation from said transalkylation product stream a lower boiling fraction comprising benzene and benzene co-boilers and a higher boiling fraction comprising toluene and having a substantial absence of benzene co-boilers;

d. recycling at least a portion of the lower boiling fraction from step c to step b sufficient to maintain a benzene to total aromatics mole ratio to step b at least about 0.2:1, preferably at least about 0.3:1, and in some preferred embodiments, at least about 0.45:1;

e. subjecting at least a portion of the higher boiling fraction from step c to disproportionation conditions including the presence of a disproportionation catalyst to provide a disproportionation product containing benzene, toluene, $C_8$ aromatics and less than about 100, preferably less than about 40, parts per million-mass (ppm-mass) benzene co-boilers; and f. separating by fractionation from at least a portion of the disproportionation product a lower boiling fraction comprising benzene and less than about 5000, preferably less than 2000, and most preferably less than about 1500, ppm-mass $C_6$ and $C_7$ non-aromatics and a higher boiling fraction comprising $C_8$ aromatics.

In preferred embodiments of the invention, at least a portion of the higher boiling fraction comprising $C_8$ aromatics is subjected to a separation to selectively remove one or more of para-xylene and ortho-xylene as xylene products and provide a non-equilibrium mixture of $C_8$ aromatics. The non-equilibrium mixture of $C_8$ aromatics is subjected to xylene isomerization conditions including the presence of isomerization catalyst to provide an isomerization product containing benzene and a greater concentration of said one or more xylene isomers selectively removed. The isomerization product is separated by fractionation into a lower boiling, benzene-containing fraction at least a portion of which is recycled to step b and a higher boiling $C_8$ aromatics-containing fraction at least a portion of which is recycled to the separation to selectively remove one or more of para-xylene and ortho-xylene.

Another broad aspect of the processes of this invention pertains to the operation of a catalytic transalkylation process in which benzene and toluene are recovered from the transalkylation product and recycled. Thus a transalkylation loop is provided. This broad aspect comprises:

a. passing a lighter aromatic stream containing at least one of benzene and toluene and a heavier aromatic stream containing $C_9$ and $C_{10}$ aromatics to a transalkylation zone;

b. subjecting said lighter aromatic stream and said heavier aromatic stream in said transalkylation zone to transalkylation conditions including the presence of a metal-stabilized transalkylation catalyst to provide a transalkylation product stream having a greater concentration of toluene and $C_8$ aromatics;

c. separating by fractionation from said transalkylation product stream a lower boiling fraction comprising benzene and at least about 10, preferably at least about 20, and sometimes up to about 80, say, 20 to 50, mass percent of the toluene in transalkylation product stream and a higher boiling fraction comprising toluene and $C_8$ aromatics;

d. recycling at least a portion of the lower boiling fraction from step c to step b sufficient to maintain a benzene to total aromatics mole ratio to step b at least about 0.2:1, preferably at least about 0.3:1, and in some preferred embodiments, at least about 0.45:1.

Another broad aspect of the processes of this invention pertains to the disproportionation processes wherein the toluene recycle to the disproportionation reaction zone contains at least about 5, and often between about 10 and 20, mass percent benzene. In this manner, the species of benzene co-boilers that are higher in boiling are maintained in the disproportionation loop thus enhancing the purity of the benzene product obtainable from the disproportionation reaction. These processes comprise:

a. distilling a feedstock comprising toluene and $C_8$ aromatics to provide a lighter fraction enriched in toluene and a heavier fraction enriched in $C_8$ aromatics;

b. subjecting at least a portion of the lighter fraction containing toluene to toluene disproportionation conditions including the presence of catalyst to provide a reaction effluent containing $C_8$ aromatics, toluene and benzene and also containing benzene co-boilers;

c. distilling the reaction effluent to provide a lower boiling fraction rich in benzene and a higher boiling fraction rich in toluene and $C_8$ aromatics and also containing up to about 5, preferably between about 0.1 to 1, mass percent benzene; and d. passing the higher boiling fraction of step (c) to step (a), wherein the lighter fraction enriched in toluene contains benzene.

In preferred embodiments, the lower boiling fraction is distilled to provide a lower boiling fraction containing benzene co-boilers that have boiling points below that of benzene and a higher boiling, benzene-containing fraction having a benzene purity of at least about 99.8 mass percent. In a further embodiment, the feedstock to the disproportionation process is derived from a transalkylation process, and intermittently or continuously a portion of the lighter fraction from step (a) is passed to the transalkylation process.

The invention also pertains to apparatus for conducting the processes of the invention. In one aspect, the integrated apparatus for co-producing xylene and pure benzene comprises:

a. a transalkylation reaction loop containing at least one transalkylation reaction zone containing transalkylation catalyst, said transalkylation zone being adapted to receive feed comprising lower aromatics comprising at least one of benzene and toluene and higher aromatics comprising $C_9$+ aromatics and having a reactor effluent port, a benzene column in fluid communication with the reactor effluent port of said transalkylation reactor and adapted to provide a benzene-containing lower boiling fraction and a higher boiling fraction containing toluene and $C_8$ aromatics, and a fluid communication line from said benzene column to said transalkylation reaction zone adapted to supply at least a portion of the lower boiling fraction to said transalkylation zone;

b. a disproportionation loop containing a toluene distillation column being adapted to received said higher boiling fraction from the benzene column of the transalkylation loop, said toluene distillation column adapted to provide a toluene-containing lower boiling fraction and a $C_8$ aromatics-containing higher boiling fraction, a disproportionation reaction zone containing catalyst for disproportionating toluene to $C_8$ aromatics and benzene, said disproportionation reaction zone being adapted to receive as feed the lower boiling fraction from said toluene distillation column and containing a reactor effluent port, and a benzene distillation column in fluid communication with the reactor effluent port of said disproportionation reactor, said benzene distillation column being adapted to provide a lower boiling benzene-containing fraction and a higher boiling toluene and $C_8$ aromatics-containing fraction, in which the benzene distillation column is in fluid communication with the toluene column for supplying the higher boiling toluene and $C_8$ aromatics-containing fraction to the toluene column; and c. a fluid communication line between the transalkylation loop and the disproportionation loop adapted to supply intermittently or continuously a portion of the lower boiling toluene-containing fraction from the toluene column of the transalkylation loop to the disproportionation loop.

In the preferred apparatus of the invention, the fluid communication line of element (c) is in fluid communication with the transalkylation reactor. In another preferred embodiment, the apparatus further comprises:

d. a xylene recovery and isomerization loop containing a xylene distillation assembly adapted to receive the $C_8$ aromatics-containing higher boiling fraction from the disproportionation loop and provide a lower boiling $C_8$ aromatics fraction and at least one higher boiling fraction containing $C_9+$ aromatics, said xylene distillation assembly being in fluid communication with the transalkylation reactor and adapted to provide $C_9$ aromatics-containing fraction to the transalkylation reactor, a selective xylene removal zone in fluid communication with the xylene distillation assembly and adapted to receive the lower boiling $C_8$ aromatics-containing fraction and adapted to provide at least one substantially pure xylene isomer stream and a stream depleted of said xylene isomer, a xylene isomerization zone in fluid communication with the xylene recovery zone, said xylene isomerization zone containing isomerization catalyst and being adapted to provide an isomerizate, a lower aromatics distillation assembly in fluid communication with the xylene isomerization zone to receive the isomerate and adapted to provide a lower boiling fraction containing benzene and toluene and a higher boiling fraction containing $C_8$ aromatics, said lower aromatics distillation assembly being in fluid communication with the transalkylation loop to provide at least a portion of the lower boiling fraction to the transalkylation loop and being in fluid communication with the xylene distillation assembly to provide the higher boiling fraction to the xylene distillation assembly.

DETAILED DESCRIPTION OF THE INVENTION

Figure 1:
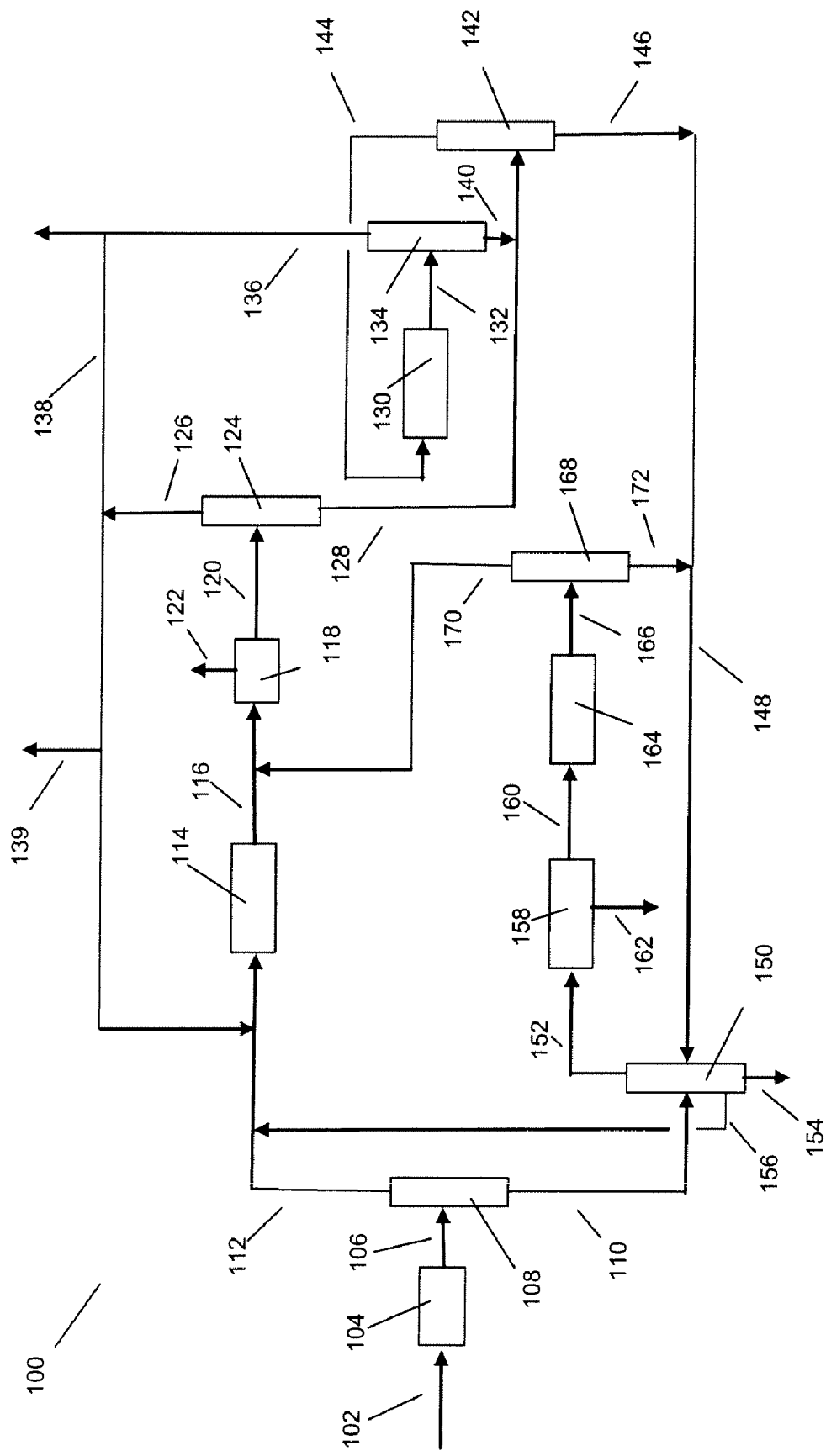
FIG. 1 is a schematic depiction of an apparatus useful in conducting the processes of this invention.

With reference to FIG. 1, 100 generally designates an apparatus in accordance with this invention. An aromatics-containing feed stream from a reformer is supplied by line 102 to treater 104. The composition of the feed is often within the ranges set forth in Table 1.

TABLE 1

| Component | Typical Range, mass-% | Preferred Range, mass-% |
| --- | --- | --- |
| Aliphatics, $C_6$ and lower | 0-20 | 2-15 |
| Aliphatics, $C_7$ and $C_8$ | 3-12 | 3-10 |
| Aliphatics, above $C_8$ | 0-5 | 0-2 |
| Benzene | 1-20 | 1-10 |
| Toluene | 10-40 | 15-30 |
| $C_8$ aromatics | 10-50 | 25-40 |
| $C_9$ aromatics | 0-20 | 10-15 |
| $C_{10}$ and above aromatics | 0-10 | 1-7 |

Treater 104 may be any suitable unit operation for reducing olefins such as a clay treater or selective hydrogenation. Treater 104 is optional and its need will depend upon the nature of the feed stream.

The treated feed stream is passed via line 106 to reformate splitter 108. From reformate splitter 108 is provided an overhead containing toluene and lighter boiling components which exits via line 112 and a bottoms fraction containing xylenes, ethylbenzene, and higher boiling components. The bottom fraction is withdrawn via line 110.

The overhead in line 112 is directed to transalkylation reactor 114. Reactor 114 contains transalkylation catalyst that is tolerant of aliphatics and heavy aromatics such as $C_{10}$ aromatics. The preferred catalyst is a metal stabilized transalkylation catalyst. Such catalyst comprises a zeolite component, a metal component, and an inorganic oxide component. The zeolite component typically is either a pentasil zeolite, which include the structures of MFI, MEL, MTW, MTT and FER (IUPAC Commission on Zeolite Nomenclature) or MWW or a beta zeolite or a mordenite. Preferably it is mordenite zeolite. The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 mass-percent, with the range from about 0.1 to about 3 mass-percent being preferred, and the range from about 0.1 to about 1 mass-percent being highly preferred. Suitable zeolite amounts in the catalyst range from about 1 to about 99 mass-percent, preferably between about 10 to about 90 mass-percent, and more preferably between about 25 to about 75 mass-percent. The balance of the catalyst is composed of inorganic oxide binder, preferably alumina. One transalkylation catalyst for use in the present invention is disclosed in U.S. Pat. No. 5,847,256, the teachings of which are incorporated herein by reference.

Conditions employed in transalkylation reactor 114 normally include a temperature of from about 200° to about 540° C. and moderately elevated pressures broadly ranging from about 100 kPa to 10 MPa absolute. The transalkylation reaction can be effected over a wide range of space velocities, with higher space velocities effecting a higher ratio of para-xylene at the expense of conversion. Liquid hourly space velocity generally is in the range of from about 0.1 to about 20 hr$^{-1}$. The feedstock is preferably transalkylated in the vapor phase and in the presence of hydrogen. For liquid phase transalkylation, the adding of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio.

In transalkylation reactor, benzene and toluene are transalkylated with $C_9$ and $C_{10}$ aromatics to make toluene and $C_8$ aromatics. As will be discussed later, recycle benzene and toluene are directed to transalkylation reactor 114 as is a $C_9$ and $C_{10}$ aromatics containing stream. The transalkylation product which is enriched in toluene and $C_8$ aromatics is passed via line 116 to stripper 118. Stripper 118 provides a lights stream 122 and which can also serve as a purge. Lights stream 122 may be used for any suitable purpose including being used as fuel. The liquid phase from stripper 118 is withdrawn via line 120 for fractionation in benzene column 124.

Benzene column 124 is preferably operated to provide an overhead containing substantially all the benzene and $C_6$ naphthenes contained in the liquid phase. The overhead is directed via line 126 to benzene header 138 for recycle to transalkylation reactor 114. Because the overhead from benzene column 124 is recycled to transalkylation reactor 114, the presence of toluene in the overhead is tolerable. If desired, a purge may be alternatively or in addition taken from line 138 via line 139 to prevent undue build-up of benzene co-boilers in the transalkylation loop. Often, the content of benzene co-boilers in line 138 is less than about 10, preferably less than about 5, mass percent. For purposes of this calculation, benzene co-boilers are total $C_6$ non-aromatics. The bottoms stream of benzene column 124 contains toluene, $C_8$ and higher aromatics, and $C_7$ and higher aliphatics including paraffins and naphthenes.

Table 2 below summarizes the typical compositions (mass percent) of the overhead and the bottoms stream of benzene column 124.

TABLE 2

| Component | Benzene column overhead | | Benzene column bottoms | |
|---|---|---|---|---|
| | Typical | Preferred | Typical | Preferred |
| Benzene | 60-100 | 75-90 | 0-0.5 | 0-0.1 |
| $C_6$ and lower aliphatics | 0-3 | 0-1 | >1000 ppm-mass | >100 ppm-mass |
| Toluene | 0-40 | 10-25 | 40-90 | 50-80 |
| $C_7$ and higher aliphatics | 0-3 | 0-0.1 | 3-15 | 3-10 |
| $C_8$ aromatics | 0-1 | 0-0.1 | 10-50 | 20-40 |
| $C_9$ and higher aromatics | 0-0.5 | 0-0.1 | 0-25 | 5-25 |

The bottoms fraction from benzene column 124 is passed via line 128 to toluene column 142. $C_8$ aromatics and other heavier components are provided as a bottoms stream and xylenes are recovered therefrom. A toluene-containing overhead is withdrawn via line 144 and passed to disproportionation reactor 130 containing catalyst.

In disproportionation reactor 130 toluene is disproportionated to benzene and to $C_8$ aromatics. The disproportionation catalyst comprises a molecular sieve and a refractory inorganic oxide. The preferred molecular sieves are zeolitic aluminosilicates, or zeolites, which may be any of those which have a $Si:Al_2$ ratio greater than about 10, preferably greater than 20, and a pore diameter of about 5 to 8 Angstroms. Specific examples of zeolites which can be used are the MFI, MEL, EUO, FER, MFS, MTT, MTW, TON, TWW, MOR and FAU types of zeolites. Pentasil zeolites MFI, MEL, MTW and TON are preferred, and MFI-type zeolites, often designated ZSM-5, are especially preferred.

Preferably the zeolitic aluminosilicate, or zeolite, has an enhanced surface silicon content, i.e., the proportion of silicon at the surface of the zeolite is greater than the proportion in the bulk of the zeolite. The "surface" is defined for purposes of the present invention as a layer at the external surface of the zeolite which is less than about 100 angstroms in depth, and usually about 10 angstroms or less in depth. Optimally the silicon/aluminum ratio, expressed as $Si/Al_2$, is increased by about 5 or more at the surface of the zeolite relative to the ratio in the bulk of the zeolite. The catalysts are usually prepared with a refractory binder or matrix. Suitable binders include inorganic oxides such as one or more of alumina, magnesia, zirconia, chromia, titania, boria, thoria, zinc oxide and silica. A preferred binder or matrix component is a phosphorus-containing alumina (hereinafter referred to as aluminum phosphate). The amount of zeolite present in the bound catalyst can vary considerably but usually is present in an amount from about 30 to 90 mass percent and preferably from about 50 to 80 mass percent of the catalyst. In a preferred embodiment, the catalyst consists essentially of the zeolite and binder.

Advantageous disproportionation catalysts have an X-ray powder diffraction pattern such that the ratio of peak intensities at respective two-θ Bragg angle positions of about 48.5:46.5 is at least about 1.1 and the ratio of peak intensities at respective two-θ Bragg angle values of about 48.5:47.5 is at least about 1.0.

It is within the scope of the invention that the catalyst contains a metal component, preferably selected from components of the group consisting of gallium, rhenium and bismuth. Preferably, however, the catalyst contains no metal component.

Optionally, the catalyst may be subjected to precoking in order to increase the proportion of paraxylene in the $C_8$ aromatics product. Further details relative to precoking are disclosed in U.S. Pat. No. 4,097,543, incorporated herein by reference.

Conditions employed for disproportionation typically include a temperature of from about 200° to 600° C., and preferably from about 250° to 575° C. The temperature required to maintain the desired degree of conversion will increase as the catalyst gradually loses activity during processing. Normal end-of-run temperatures may therefore exceed start-of-run temperatures by 65° C. or more. The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of para-xylene at the expense of conversion. Weight hourly space velocity generally is the range of from about 0.2 to 10 $hr^{-1}$.

The disproportionation product from reactor 130 is passed via line 132 to benzene column 134 for fractionation. Not shown is a stabilizer column that removes lights, e.g., hydrogen and up to $C_5$ alkanes from the disproportionation product. An overhead containing benzene is withdrawn from benzene column 134 via line 136 and a bottoms fraction containing toluene and $C_8$ aromatics is withdrawn via line 140. A portion of the overhead is line 136 can be recycled to transalkylation reactor, if desired, via benzene header 138.

As the $C_6$ and lighter aliphatics have been removed from the feed to disproportion reactor 130 by benzene column 124, highly pure benzene can be obtained as overhead from benzene column 134 without the need for extraction. Depending upon the conditions of the disproportionation, including the type of catalyst employed, some generation of benzene co-boilers will commonly occur during the disproportionation. Nevertheless, by isolating benzene co-boilers in the transalkylation operation, a higher purity benzene product can be obtained. As shown, benzene column 134 provides the highly pure benzene product. If desired, the fractionation to provide the benzene product can be done in two stages, the first providing a benzene stream suitable for recycle via benzene header 138 to transalkylation reactor 114, and the second providing the highly pure benzene. The typical compositions of the highly pure benzene obtained by use of the processes of this invention are provided in Table 3.

TABLE 3

| | Benzene Purity | |
|---|---|---|
| Component | Typical, mass-% | Preferred, mass-% |
| Benzene | 99.5 to 99.999 | 99.85-99.999 |
| $C_6$+ naphthenes | >0.2 | >0.1 |
| Toluene | >0.2 | >0.1 |
| Other | >0.1 | >0.05 |

The bottoms fraction from benzene column 134 is passed via line 140 to toluene column 142. A toluene-containing overhead is withdrawn via line 144 to disproportionation reactor 130. A bottoms fraction contains $C_8$ aromatics and is passed from toluene column 142 via line 146 to $C_8$ header 148 to xylene column 150.

Xylene column 150 is fed not only the bottoms fraction from toluene column but also from reformate splitter 108. As depicted, xylene column 150 provides a $C_8$ aromatics containing overhead which is withdrawn via line 152, a bottoms fraction primarily containing $C_{11}$ aromatics and heavier components which is withdrawn via line 154 and a side-cut rich in $C_9$ and $C_{10}$ aromatics. This side cut is passed to transalkylation reactor 114 via line 156. Another embodiment would be to send the whole bottoms fraction in xylene column 150 to transalkylation reactor 114 instead of just the side cut. A separate column to remove coke precursors such as methyl indan and naphthalene are typically not needed since the catalyst used for transalkylation con tolerate such precursors.

If ortho-xylene is to be produced in the complex, xylene column 150 is typically designed to make a split between meta and ortho-xylene. An ortho-xylene-containing fraction from xylene column 150 would then be sent to an ortho-xylene column (not shown) where high purity ortho-xylene product is recovered overhead. Material from the lower part of the ortho-xylene column would be a stream rich in $C_9$ and $C_{10}$ alkylaromatics that could be sent to transalkylation reactor 114.

The overhead from xylene column 150 is passed to para-xylene separation zone 158 via line 152. Para-xylene separation zone may be based on a fractional crystallization process or an adsorptive separation process, both of which are well known in the art, and preferably is based on the adsorptive separation process. Such adsorptive separation can recover over 99 mass-percent pure para-xylene in a line 162. At least a portion of any residual toluene in the feed to the separation unit is extracted along with the para-xylene, fractionated out in a finishing column within the unit, and then optionally recycled to transalkylation reactor 114 or benzene column 124. Thus, the raffinate from the paraxylene separation zone 158 is almost entirely depleted of para-xylene, to a level usually of less than 1 mass-percent. The raffinate is sent via a line 160 to alkylaromatics isomerization reactor 164, where additional para-xylene is produced by reestablishing an equilibrium or near-equilibrium distribution of xylene isomers.

In alkylaromatic isomerization reactor 164, the raffinate stream is contacted with an isomerization catalyst under isomerization conditions. The isomerization catalyst is typically composed of a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a nonzeolitic molecular sieve. The zeolitic aluminosilicate (or zeolite) component typically is either a pentasil zeolite, which include the structures of MFI, MEL, MTW, MTF and FER (IUPAC Commission on Zeolite Nomenclature), MWW, a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992).

The metal component typically is a noble metal component, and may include an optional base metal modifier component in addition to the noble metal or in place of the noble metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the isomerization catalyst range from about 0.01 to about 10 mass-percent, with the range from about 0.1 to about 3 mass-percent preferred. Suitable zeolite amounts in the catalyst range from about 1 to about 99 mass-percent, preferably between about 10 to about 90 mass-percent, and more preferably between about 25 to about 75 mass-percent. The balance of the catalyst is composed of inorganic oxide binder, typically alumina. One isomerization catalyst for use in the present invention is disclosed in U.S. Pat. No. 4,899,012, the teachings of which are incorporated herein by reference.

Typical isomerization conditions include a temperature in the range from about 0° to about 600° C. and a pressure from about 100 kPa to about 6 MPa absolute. The liquid hourly hydrocarbon space velocity of the feedstock relative to the volume of catalyst is from about 0.1 to about 30 $hr^{-1}$. The hydrocarbon contacts the catalyst in admixture with a gaseous hydrogen at a hydrogen-to-hydrocarbon mole ratio of from about 0.5:1 to 15:1 or more, and preferably a ratio of from about 0.5 to 10. If liquid phase conditions are used for isomerization, then no hydrogen is added to the unit.

The effluent from isomerization reactor is sent via a line 166 to a deheptanizer column 168. A bottoms stream in a line 172 from deheptanizer column 168 contains $C_8$ aromatics including para-xylene. This bottoms stream may optionally be treated to remove olefins (e.g., by a dedicated olefin saturation unit or by feeding the bottoms stream to treater 104). If the catalyst used in the isomerization reactor 164 is the ethylbenzene dealkylation type, then olefin saturation is typically not required. As shown, deheptanizer bottoms stream in line 172 is passed to $C_8$ header 148 for recycle back to xylene column 150.

The overhead from the deheptanizer column 168 is recycled to transalkylation reactor 114. Especially where the isomerization catalyst dealkylates ethylbenzene, the overhead will contain benzene in addition to toluene. As $C_6$ naphthenes may have been generated during isomerization, the processes of this invention by passing the deheptanizer column overhead to the transalkylation section, enable benzene column 134 to provide the sought high purity benzene without the necessity for an extraction unit operation.

The amount of highly pure benzene that can be obtained from benzene column 134 is in relationship to the amount of toluene consumed in the disproportionation of disproportionation reactor 114. An important feature of the processes of this invention is that transalkylation reactor 114 is operated to enhance the production of toluene such that desirable amounts of highly pure benzene can be obtained from benzene column 134. This is achieved by both operating the transalkylation in transalkylation reactor 114 with a relatively high ratio of benzene to total aromatics, and by feeding both $C_9$ and $C_{10}$ aromatics to transalkylation reactor 114. Consequently, the mole ratio of highly pure benzene available from benzene column 134 (including any benzene that may be recycled to transalkylation reactor 114) to para-xylene product (assuming no other $C_8$ aromatic product) in line 162 is between about 0.1:1 to 0.8:1. It is understood that this ratio will change depending upon how much $C_8$ aromatics are contained in the feed stream in line 102 and whether orthoxylene is recovered as a product. Typically the mole ratio of benzene to total aromatics fed to transalkylation reactor is from about 0.2:1 to 0.6:1, preferably about 0.25:1 to 0.5:1. Table 4 provides the typical feed compositions to transalkylation reactor 114, and Table 5 provides the typical compositions of the feed to benzene column 124.

TABLE 4

| Component in Transalkylation Feed | Typical Ranges, mass-% | Preferred ranges, mass-% |
| --- | --- | --- |
| Benzene | 10-80 | 20-75 |
| $C_6$ and lower aliphatics | 2-20 | 2-10 |
| Toluene | 0-60 | 0-20 |
| $C_7$ and higher aliphatics | 1-10 | 1-5 |
| $C_8$ aromatics | 0-20 | 0-5 |
| $C_9$ aromatics | 0-80 | 0-70 |
| $C_{10}$ aromatics | 0-20 | 0-15 |
| Other ($C_{11+}$) | 0-5 | 0-3 |

TABLE 5

| Component in Benzene Column Feed | Typical Ranges, mass-% | Preferred ranges, mass-% |
| --- | --- | --- |
| Benzene | 2-60 | 5-40 |
| $C_6$ and lower aliphatics | 2-20 | 2-10 |
| Toluene | 5-80 | 20-70 |
| $C_7$ and higher aliphatics | 1-10 | 1-5 |
| $C_8$ aromatics | 5-60 | 20-50 |
| $C_9$ aromatics | 0-30 | 2-25 |
| $C_{10}$ aromatics | 0-15 | 0-10 |
| Other | 0-5 | 0-1 |

Figure 2:
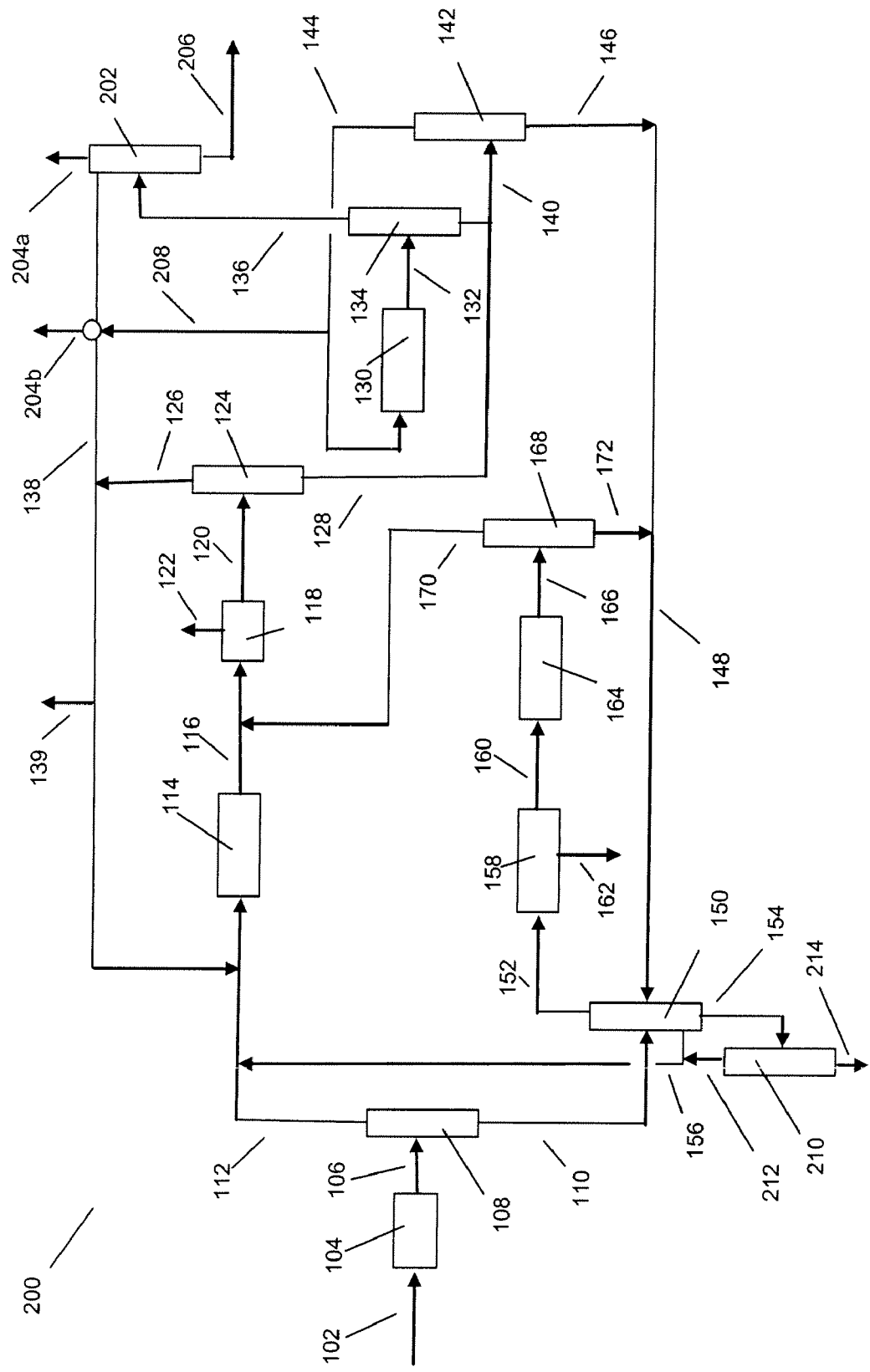
FIG. 2 is a schematic depiction of a preferred apparatus useful in conducting the processes of this invention where a benzene product having a purity of at least about 99.8 mass percent is desired.

FIG. 2 depicts an apparatus, generally indicated by the numeral 200, that is preferred for achieving a benzene coproduct having a purity of at least about 99.85 mass percent. In this Figure, like components are designated with the same numbers as in FIG. 1.

In this apparatus the overhead from benzene column 134 is passed via line 136 to benzene purification column 202. While two distillation columns are depicted, it is within the broad scope of the invention that a single vessel can perform the same function. As shown, a lights overhead is withdrawn from benzene purification column 202 via line 204a. This stream contains non-aromatics having boiling points lower than benzene. A purified benzene stream is recovered from the bottoms of column 202 and is withdrawn via line 206. And a fraction containing benzene and some lighter benzene coboilers is withdrawn from the upper portion of column 202 into line 138. Intermittently or continuously a portion or all of this fraction can be recycled to the transalkylation reaction system, and that portion not recycled can be exhausted via line 204b.

In some instances, it may not be desired to recycle any of the fraction contained in line 138, especially where the disproportionation catalyst generates substantial amounts of lighter benzene co-boilers, to prevent undue build-up of these lighter benzene co-boilers in the transalkylation loop or require a larger purge from the transalkylation loop.

Benzene column 134 is preferably operated such that less than about 5, preferably about 0.1 to 1, mass percent of the benzene fed to it is contained in the bottoms fraction. This operation effectively removes those of the benzene co-boilers having a higher boiling point. The bottoms fraction from benzene column 134 is passed to toluene column 142 where the contained benzene is fractionated into the overhead for recycle to reactor 130. Hence, benzene values are not lost from the integrated process of this invention. Benzene purification column 202 is preferably operated such that at least about 2, preferably between about 5 and 25, mass percent of the benzene fed to it is contained in the overhead fraction, and the bottoms fraction has a benzene purity of at least about 99.5, preferably at least 99.85, mass-percent.

Line 208 is adapted to intermittently or continuously remove a portion of the toluene-containing stream in line 144 in an amount sufficient to maintain the benzene and benzene co-boiler content in the disproportionation loop at desirable levels. Preferably, the benzene co-boiler content in line 144 is maintained at less than about 10 mass percent. The benzene content of the stream in line 144 is generally in less than about 15, preferably less than about 10, mass percent. All or a portion of the fluid in line 208 can be removed via line 204b.

As depicted in FIG. 2, xylene column 150 provides a bottoms fraction. This bottoms fraction from xylene column is passed via line 154 to heavies column 210. The heavies column recovers $C_{10}$ aromatics in the bottoms fraction which is passed via line 212 to line 156 as a portion of the heavies feed to the transalkylation section. Line 214 exhausts a bottoms fraction from heavies column 210.

Once understanding the principles of this invention, the specific design of the various distillation columns referenced herein, such as diameter, number of plates and type of packing or tray, as well as their operating parameters such as bottoms temperature and reflux ratio, are within the skill in the art.

The invention claimed is:

1. A process for transalkylation and disproportionation comprising:
   a. passing a lighter aromatic stream containing at least one of benzene and toluene and a heavier aromatic stream containing $C_9$ and $C_{10}$ aromatics to a transalkylation zone;
   b. subjecting said lighter aromatic stream and said heavier aromatic stream in said transalkylation zone to transalkylation conditions including the presence of a metal-stabilized transalkylation catalyst to provide a transalkylation product stream having a greater concentration of toluene and $C_8$ aromatics;
   c. separating by fractionation from said transalkylation product stream a lower boiling fraction comprising benzene and at least about 10 mass percent of the toluene in transalkylation product stream and a higher boiling fraction comprising toluene and $C_8$ aromatics;

d. recycling at least a portion of the lower boiling fraction from step c to step b sufficient to maintain a benzene to total aromatics mole ratio to step b at least about 0.2:1;

e. passing at least a portion of the higher boiling fraction from step c to a disproportionation zone at disproportionation condition including the presence of a disproportionation catalyst to generate a disproportion product;

f. subjecting at least a portion of the higher boiling fraction comprising C8 aromatics of step c to a separation to selectively remove one or more of para-xylene and ortho-xylene as xylene products and provide a non-equilibrium mixture of C8 aromatics;

g. subjecting the non-equilibrium mixture of C8 aromatics to xylene isomerization conditions including the presence of isomerization catalyst to provide an isomerization product containing benzene and a greater concentration of said xylene isomer selectively removed in step f; and h. separating the isomerization product by fractionation into a lower boiling, benzene-containing fraction at least a portion of which is recycled to step b and a higher boiling C8 aromatics-containing fraction at least a portion of which is recycled to step f.

2. The process of claim 1 wherein the disproportionation catalyst has an essential absence of metal promoter.

3. The process of claim 1 wherein the metal stabilizing the metal-stabilized transalkylation catalyst comprises rhenium.

4. The process of claim 3 wherein the metal stabilized transalkylation catalyst comprises rhenium and MOR-type zeolite.

5. The process of claim 1 wherein the isomerization catalyst is active for the dealkylation of ethylbenzene.

6. The process of claim 1 wherein the aromatic feedstock contains $C_9$ and $C_{10}$ aromatics and at least a portion of said $C_9$ and $C_{10}$ aromatics are separated by distillation and fed to step b as at least a portion of the $C_9$ and $C_{10}$ aromatics for providing transalkylation conditions.

* * * * *